(12) United States Patent
Crank

(10) Patent No.: US 9,017,282 B2
(45) Date of Patent: Apr. 28, 2015

(54) NEEDLELESS INJECTION DEVICE COMPONENTS, SYSTEMS, AND METHODS

(71) Applicant: AMS Research Corporation, Minnetonka, MN (US)

(72) Inventor: Justin M. Crank, Maple Grove, MN (US)

(73) Assignee: AMS Research Corporation, Minnetonka, MN (US)

( * ) Notice: Subject to any disclaimer, the term of this patent is extended or adjusted under 35 U.S.C. 154(b) by 141 days.

(21) Appl. No.: 13/728,472

(22) Filed: Dec. 27, 2012

(65) Prior Publication Data

US 2013/0123686 A1 May 16, 2013

Related U.S. Application Data

(60) Division of application No. 12/839,956, filed on Jul. 20, 2010, now Pat. No. 8,366,657, which is a continuation-in-part of application No. PCT/US2009/006382, filed on Dec. 4, 2009.

(60) Provisional application No. 61/226,906, filed on Jul. 20, 2009, provisional application No. 61/226,913, filed on Jul. 20, 2009, provisional application No. 61/120,101, filed on Dec. 5, 2008, provisional application No. 61/120,163, filed on Dec. 5, 2008, provisional application No. 61/122,884, filed on Dec. 16, 2008.

(51) Int. Cl.
*A61M 5/30* (2006.01)
*A61M 5/145* (2006.01)
*A61M 5/315* (2006.01)
*A61B 1/015* (2006.01)
*A61M 5/20* (2006.01)

(52) U.S. Cl.
CPC .............. *A61M 5/3007* (2013.01); *A61B 1/015* (2013.01); *A61M 5/1452* (2013.01); *A61M 5/204* (2013.01); *A61M 5/30* (2013.01); *A61M 5/31553* (2013.01); *A61M 5/3156* (2013.01); *A61M 5/31563* (2013.01); *A61M 2205/505* (2013.01)

(58) Field of Classification Search
USPC ..................................................... 604/68, 70
See application file for complete search history.

(56) References Cited

U.S. PATENT DOCUMENTS 4,093,108 A 6/1978 Hein et al.
4,130,119 A 12/1978 Sessions et al.
(Continued)

FOREIGN PATENT DOCUMENTS

WO WO9616606 A1 6/1996
WO WO9736625 A1 10/1997
(Continued)

*Primary Examiner* — Aarti B Berdichevsky
(74) *Attorney, Agent, or Firm* — Kagen Binder, PLLC

(57) ABSTRACT

A high-pressure fluid injection system, which includes a rechargeable injection chamber with a proximal end, a distal end, and an internal opening extending from the proximal end to the distal end, a plunger slideably engaged with the internal opening of the injection chamber, an injection tube extending from the distal end of the injection chamber and in fluidic communication with the internal opening of the injection chamber, and a check valve between the proximal and distal ends of the injection chamber. The internal opening includes a high-pressure zone adjacent to the check valve and having a first diameter, and a low-pressure zone proximal to the high-pressure zone and having a second diameter that is larger than the first diameter.

8 Claims, 5 Drawing Sheets

(56) References Cited

U.S. PATENT DOCUMENTS

| | | | |
|---|---|---|---|
| 4,742,817 A | 5/1988 | Kawashima et al. | |
| 4,946,442 A | 8/1990 | Sanagi | |
| 5,007,897 A | 4/1991 | Kalb | |
| 5,116,313 A | 5/1992 | McGregor | |
| 5,261,889 A | 11/1993 | Laine et al. | |
| 5,336,178 A | 8/1994 | Kaplan | |
| 5,693,016 A | 12/1997 | Gumaste et al. | |
| 5,840,062 A | 11/1998 | Gumaste et al. | |
| 6,203,533 B1 | 3/2001 | Ouchi | |
| 6,210,378 B1 | 4/2001 | Ouchi | |
| 6,238,336 B1 | 5/2001 | Ouchi | |
| 6,280,413 B1 | 8/2001 | Clark et al. | |
| 6,400,980 B1 | 6/2002 | Lemelson | |
| 6,537,205 B1 | 3/2003 | Smith | |
| 6,547,767 B1 | 4/2003 | Moein | |
| 6,641,553 B1 | 11/2003 | Chee et al. | |
| 6,905,475 B2 | 6/2005 | Hauschild et al. | |
| 7,749,156 B2 | 7/2010 | Ouchi | |
| 2001/0034507 A1* | 10/2001 | Kirchhofer et al. | 604/211 |
| 2002/0082546 A1* | 6/2002 | Crank et al. | 604/48 |
| 2003/0089743 A1* | 5/2003 | Py et al. | 222/386 |
| 2003/0163111 A1 | 8/2003 | Daellenbach | |
| 2004/0030320 A1 | 2/2004 | Chee et al. | |
| 2004/0162528 A1 | 8/2004 | Horvath et al. | |
| 2005/0192530 A1 | 9/2005 | Castellano | |
| 2005/0228225 A1 | 10/2005 | Hauschild et al. | |
| 2005/0263543 A1* | 12/2005 | Py et al. | 222/386 |
| 2006/0129125 A1 | 6/2006 | Copa et al. | |
| 2007/0167921 A1 | 7/2007 | Burren et al. | |
| 2007/0225554 A1 | 9/2007 | Maseda et al. | |
| 2008/0114203 A1 | 5/2008 | Crank | |
| 2008/0119784 A1 | 5/2008 | Roychowdhury | |
| 2008/0119823 A1 | 5/2008 | Crank | |
| 2008/0262436 A1* | 10/2008 | Olson | 604/198 |
| 2008/0294096 A1* | 11/2008 | Uber et al. | 604/66 |
| 2009/0124974 A1 | 5/2009 | Crank et al. | |
| 2009/0312696 A1 | 12/2009 | Copa et al. | |
| 2011/0015614 A1 | 1/2011 | Rykhus, Jr. et al. | |
| 2011/0264036 A1* | 10/2011 | Crank et al. | 604/68 |

FOREIGN PATENT DOCUMENTS

| | | |
|---|---|---|
| WO | WO0040279 A1 | 7/2000 |
| WO | WO0066199 A1 | 11/2000 |
| WO | WO0136029 A1 | 5/2001 |
| WO | WO0207812 A2 | 1/2002 |
| WO | WO2004071612 A2 | 8/2004 |
| WO | WO2005094921 A1 | 10/2005 |
| WO | WO2006057604 A1 | 6/2006 |
| WO | WO2006063180 A2 | 6/2006 |
| WO | WO2006076699 A1 | 7/2006 |
| WO | WO2006084821 A2 | 8/2006 |
| WO | WO2006086719 A2 | 8/2006 |
| WO | WO2007038591 A2 | 4/2007 |
| WO | WO2007079152 A2 | 7/2007 |
| WO | WO2010065126 A2 | 6/2010 |
| WO | WO2010065127 A2 | 6/2010 |
| WO | WO2010065133 A2 | 6/2010 |
| WO | WO2010074705 A2 | 7/2010 |
| WO | WO2010077271 A2 | 7/2010 |
| WO | WO2011011423 A1 | 1/2011 |

\* cited by examiner 

NEEDLELESS INJECTION DEVICE COMPONENTS, SYSTEMS, AND METHODS

CROSS-REFERENCE TO RELATED APPLICATION

The present application is a divisional application of U.S. application Ser. No. 12/839,956, filed Jul. 20, 2010, now allowed, which is a CIP of PCT/US2009/006382, filed Dec. 4, 2009, by AMS Research Corporation, entitled, DEVICES, SYSTEMS AND METHODS FOR DELIVERING FLUID TO TISSUE, which in turn claims priority to U.S. Provisional Application No. 61/120,101, filed Dec. 5, 2008, entitled INJECTION VOLUME CONTROL USING ONE OR MORE ROTATING, STEPPED STOPS; U.S. Provisional Application No. 61/120,163, filed Dec. 5, 2008, entitled MEANS OF REDUCING JET INJECTION RESPONSE TIME; and U.S. Provisional Application No. 61/122,884, filed Dec. 16, 2008, entitled MEANS OF AUTOMATING BALLOON INFLATION BY VOLUME OR PRESSURE CONTROL. The present application also claims priority under 35 U.S.C. §119(e) to U.S. Provisional Application No. 61/226,906, filed Jul. 20, 2009, entitled, HIGH-PRESSURE INJECTION CATHETER SYSTEM HAVING STEPPED DOSAGE CONTROL; and U.S. Provisional Application No. 61/226,913, filed Jul. 20, 2009, entitled, HIGH-PRESSURE INJECTION CATHETER SYSTEM WITH RECHARGEABLE INJECTION CHAMBER. Each of these above-listed applications is incorporated herein by reference in its entirety.

TECHNICAL FIELD

The present invention relates generally to the delivery of therapeutic fluids to a treatment site within a patient. More specifically, the invention relates to methods and devices for treating tissue within the human body using a pressurized injection system that accurately delivers therapeutic fluids to a desired location, such as the urinary tract of a patient.

BACKGROUND

A wide variety of medical treatments utilize the delivery and introduction of therapeutic compositions to a treatment location in a patient. In home or outpatient settings, the delivery methods used can include procedures such as oral delivery or inhalants, while in clinical or hospital types of settings, a therapeutic fluid is often injected using a needle-based system. In more complicated methods, a fluid can be delivered surgically through a tubular device, such as a catheter or endoscope, and in some cases, the surgical method can involve minimally invasive procedures.

For minimally invasive procedures, a number of systems have been developed for delivering therapeutic fluids to treatment sites within a patient that include minimally invasive, tubular delivery lumens (e.g., catheters or endoscopes) and pressurized fluid sources. In some cases, these fluid sources include a syringe-like structure that is actuated by a plunger. This plunger can be controlled via a console having control features that help the user to control the amount of pressurized fluid that is delivered to and/or expelled from the system. These systems can include needleless fluid injection systems, for example. Needleless devices and methods for treating tissue of the urinary tract are discussed, for example, in Applicants' copending application U.S. Ser. No. 12/087,231, filed Jun. 27, 2008 (Copa et al.), titled "Devices, Systems, and Related Methods for Delivery of Fluid to Tissue", and U.S. Patent Application Publication No. 2006/0129125 (Copa et al.), the entire disclosures of which are incorporated herein by reference. One area of the body in which such needleless fluid delivery systems have been known to be used is for diseases of the prostate, such as prostatitis, benign prostatic hyperplasia, and prostatic carcinoma.

Needleless fluid delivery systems can include the use of a tube-like device, such as an elongated catheter tube, which is configured to provide a jet-injection of a therapeutic fluid at a desired treatment site. Generally, a needleless injector is used to deliver the therapeutic fluid that is provided from an external reservoir that is located at a proximal end of the tube-like device. The actual fluid administration occurs at a distal end of the tube-like device. Due to the relatively long travel length of the therapeutic fluid through the tube-like device, an injector must generally be capable of pressurizing the therapeutic fluid to relatively high pressures.

For any injection or injected tissue, therapeutic agents should be delivered with minimal discomfort and procedure time, and with the best possible degree of accuracy of delivery location and delivery volume, and with uniform and accurate distribution of a fluid throughout injected tissue. Further, due to the characteristics associated with the delivery of therapeutic compositions to treatment locations in a patient, there is a need to provide improved procedures, systems, and components for fluid delivery using needleless fluid delivery systems. Such procedures, systems, and components would provide for accurate and controlled dispensing of therapeutic compositions to specific treatment locations within a patient. In particular, there exists a continuing need to provide improved devices for delivering therapeutic fluids to different tissues such as locations of the urinary tract including the bladder, bladder neck, prostate, urethra, kidneys, and ureters.

SUMMARY

The invention generally involves needleless fluid injection devices, systems, and methods. These devices and systems allow for targeted delivery of therapeutic fluids at desired anatomical tissue locations, such as locations in the male or female urinary tract, (e.g., bladder, bladder neck, kidney, ureters, urethra, prostate, etc.). The therapeutic fluids can include biologically active species and agents such as chemical and biochemical agents, for example. Exemplary devices can be designed to deliver fluid at various tissue locations, and can further deliver multiple different therapeutic fluids having varying material properties (e.g., viscosity). The devices can be capable of delivering precise amounts of fluid for injection at precise locations and at specific pressures that are adjustable depending on the fluid being administered to the location in the patient.

In one aspect of this invention, control systems are provided for controlling the inflation of a tissue tensioner or balloon for a fluid delivery system, such as for a needleless fluid injection device. In another aspect of the invention, a system for reducing the response time for jet injection of fluid is provided. In yet another aspect of the invention, systems and devices are provided for controlling the volume of fluid that is ejected from a fluid injection system, which systems include at least one stop that is selectively rotated to limit the movement of a shaft in a linear direction, thereby controlling the amount of fluid that is ejected from the system.

In another aspect of the invention, a fluid injection system is provided, which comprises a shaft comprising a proximal end, a distal end, and at least one protrusion extending from an outer surface of the shaft adjacent the proximal end, and a rotatable, stepped stop member comprising multiple flat step portions, wherein the stop member is positioned concentrically around the shaft, and wherein the shaft is linearly translatable in a distal direction for engagement of the at least one protrusion with at least one of the flat step portions.

In yet another aspect, a high-pressure fluid injection system is provided, which comprises a rechargeable injection chamber comprising a proximal end, a distal end, and an internal opening extending from the proximal end to the distal end, a plunger slideably engaged with the internal opening of the injection chamber, an injection tube extending from the distal end of the injection chamber and in fluidic communication with the internal opening of the injection chamber, and a check valve between the proximal and distal ends of the injection chamber. The internal opening comprises a high-pressure zone adjacent to the check valve and having a first diameter, and a low-pressure zone proximal to the high-pressure zone and having a second diameter that is larger than the first diameter.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
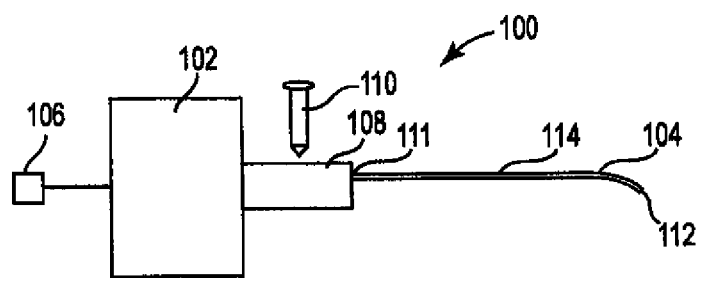
FIG. 1 is a schematic illustration of one embodiment of a needleless fluid delivery system for delivering a therapeutic fluid to a treatment location, in accordance with the invention.

The invention relates to devices and methods useful for injecting fluid into tissue for treatment. The fluid can be injected without the use of a needle and can therefore be referred to as a needleless fluid injection system. Needleless fluid injection systems of the invention can include one or more orifices that deliver fluid in the form of a stream of fluid, which may be referred to as a jet or fluid stream, at a pressure, velocity, and stream size that allow the fluid stream to pass through a tissue surface, penetrate into the bulk of the tissue below the tissue surface, and become dispersed as fluid particles within the tissue, such as in the form of a cloud of dispersed fluid particles or droplets, without a needle structure passing into the tissue. The type of tissue injected for treatment can be any amenable tissue, which can include tissue at or near the urinary tract (e.g., tissue of the prostate, kidneys, ureters, urethral tissue, bladder (including the bladder neck), etc.), or other tissues such as heart tissue, as desired.

Needleless devices of the type described herein generally include a distal end and a proximal end. As used herein, a "distal end" of a device or system refers to an end area or portion of the device or system that can be introduced internally within a patient's body during a treatment procedure, generally including the distal end of an elongate shaft or catheter tube. For example, an elongate shaft or catheter of the needleless injection systems of the invention generally includes a distal end that is the first portion of the device that is introduced into the patient for treatment. A distal end may include functional features that operate on fluid or tissue during use, such as one or more ejection orifices, delivery heads (e.g., end effectors, nozzles, etc.) that house one or more ejection orifices, a frictional tissue holding tip, tissue tensioners, lighting or other optical features, steering features, and the like.

As used herein, a "proximal end" of an exemplary needleless device or system is the end that is opposite the distal end of that device or system. To that end, each individual component of a system can include its own proximal and distal ends, while the overall system can also include proximal and distal ends. For one example, a needleless fluid injection system of the invention can include an injector body or console at a proximal end that remains external to the patient during use and an elongate shaft or catheter tube at a distal end. That is, exemplary needleless fluid delivery devices or systems can include a proximal end that includes a console, and an elongate shaft extending from a proximal end, which is in communication with the console, to a distal end. One or more injection orifices at the distal end can be in fluid communication with the console.

An exemplary console used with systems of the invention can include a housing that connects to or is otherwise (directly or indirectly) in fluid communication with an elongate shaft or catheter tube. The console can include fluid that can be pressurized by a pressure source to cause the fluid to flow through the shaft for injection into tissue at the distal end. A device can eject fluid from one or multiple ejection orifices that can be located at the distal end of the shaft or catheter tube A device can eject fluid from at least one injection orifice located at the distal end of the shaft. Optionally, multiple injection orifices may be located at one or more locations along a length of or about a circumference of a shaft distal end. Devices, systems, and methods are described herein that can be used to inject a fluid through a surface of a tissue, penetrating without the use of a needle through the tissue surface and into the bulk of the tissue, and dispersing as particles or droplets within the tissue below the tissue surface. The injected fluids may be referred to as an "injectate" or "injection fluid", which may be any type of fluid such as a therapeutic fluid. The injectate can be administered into tissue in a needleless manner, whereby the injectate is delivered as a pressurized fluid stream or jet. This contrasts with injections performed using a needle, whereby a hollow needle structure penetrates tissue to locate a hollow end of the needle within a tissue mass, below the tissue surface, after which the needle carries fluid into the bulk of the tissue and delivers the fluid at a relatively low pressure to the tissue in the form of a body or pool of fluid known as a bolus.

Referring now to the Figures, wherein the components are labeled with like numerals throughout the several Figures, and initially to FIG. 1, one preferred configuration of a needleless fluid delivery system 100 is schematically illustrated. Delivery system 100 generally includes an injection console 102, an injection chamber 108 in operative communication with the console 102, and a catheter tube or elongate shaft 104 that is also in operative communication with the console 102. The console 102 includes a user interface 106, which can be used for activating and controlling the activities of the various components of the delivery system 100. The user interface 106 can include an input means for selectively delivering a volume of pressurized fluid through the injection chamber 108. The user interface 106 may further include one or more actuatable devices, such as a foot petal, a hand activated controller, switches, buttons, and/or the like. It is also contemplated that the user interface 106 can include a touchscreen that is capable of receiving touch commands and may optionally include a display system for displaying information such as the mode of operation that is being used and/or certain operating parameters of the system.

Although console 108 can include a wide variety of features, any console used in the fluid delivery systems of the invention can generally include a housing, a pressure chamber, and a pressure source. A console can have any configuration, size, or design, ranging from a small, hand-held design to a relatively larger floor or table-mounted console. The consoles can also include separate or separable components such as a pressure chamber or injection chamber that can be attached, used for an injection procedure, and detached and optionally discarded or sterilized and reused. A shaft or catheter tube can also be attached to a console or a pressure chamber in a manner that facilitates separation and optional re-attachment or disposal.

With separable components, a shaft or injection chamber can be attached to a console housing and used to inject a first patient and/or a first injectate, and then the shaft or pressure chamber can be removed and discarded or sterilized. A second shaft or pressure chamber can then be attached to the console to treat a second patient or the first patient with second injectate or administer another treatment of the first injectate. The second patient or injectate can involve injection and treatment of the same type of tissue as the first patient or injectate, or of a new type of tissue than was treated in the first treatment. In this manner, separable and optionally disposable shaft or pressure chamber components of a needleless injection system can allow a console housing to be used multiple times to inject the same or different injectates to the same or different patients, and to the same or different types of body tissue, thereby providing an injection system that is flexible for use in a wide variety of situations and with a wide variety of fluids. Examples of system configurations, features and combinations of system features that can be useful according to the present description include U.S. Patent Application Publication No. 2006/0129125 (Copa et al.); U.S. Publication No. 2009/0312696, filed Jun. 27, 2008 (Copa et al.); PCT patent application Serial No. U.S.09/06390, filed Dec. 4, 2009 (Crank et al.), titled "Devices, Systems, and Related Methods for Delivery of Fluid to Tissue"; PCT patent application Serial No. U.S.09/06384, filed Dec. 4, 2009 (Crank), titled "Needleless Injection Device Components, Systems, and Methods"; PCT patent application Serial No. U.S.09/06383, filed Dec. 4, 2009 (Rykhus et al.), titled "Method and Apparatus for Compensating for Injection Media Viscosity in a Pressurized Drug Injection System", the entireties of which are all incorporated herein by reference.

A console can include actuating features to control distal end features, e.g., for steering a steerable distal end of a steerable shaft, to actuate ejection of fluid, to move a moveable or extendable injection shaft or one or more injection orifice relative to another shaft component such as a working shaft, optional ports to connect a console housing to auxiliary devices, electronics such as controls, optic features such as a lens, fiber optic, or electronic viewing mechanism to allow viewing through an optical feature (to view a location of delivery), and an actuating mechanism or pressure source for a tissue tensioner in the form of a mechanical tissue tensioner or an inflatable balloon. One or more attachment ports can optionally attach a console to an external and optionally remote component such as an external or remote pressure source, vacuum source, or an external or remote fluid reservoir to supply injectate or other fluid, such as to inflate a balloon. For example, a console (e.g., console housing or connector member) may have a fluid port that attaches to a source of a fluid to supply the fluid to the console, such as to a permanent or detachable pressure chamber. Embodiments of consoles can include a permanent or removable pressure chamber and a pressure source capable of pressurizing a fluid contained in the pressure chamber to cause the fluid to flow from the console, through a lumen in the shaft, and then through an injection orifice.

In embodiments of devices that involve the use of a control fluid, a pressurized control fluid can be produced by a console using any useful technique and mechanism. For example, the pressurized control fluid can be produced by a pressure source, such as any pressurized fluid source, magnetohydrodynamic power, expanding steam or gas power, or the like, with any available and useful control fluid, which may be a liquid or a gas.

Fluid can be provided to the system 100 by a fluid supply 110, which can be provided as a syringe that is manually activated, such as by physically pressing a plunger into a syringe barrel that is at least partially filled with fluid to push fluid from the syringe barrel. Alternatively, fluid supply 110 can have a different configuration than a syringe, and the fluid supply can be automatically or mechanically activated, such as with an electronic fluid supply controller or with one or more remote activation devices that can be manipulated by the user to move the plunger into and out of a syringe barrel. In yet another alternative, the fluid supply 110 is not a syringe, but instead includes a larger fluid source, such as a reservoir or other container that holds the fluid until it is provided to the injection chamber 108. Such a container can be positioned so that the fluid is gravity fed to the injection chamber, for example, or so that the fluid can be extracted using a vacuum source, for another example. With any of the different types of fluid supplies used with the systems of the invention, it is contemplated that an exact amount of fluid to be administered can be premeasured and provided to the system until that quantity of fluid is depleted and/or a predetermined amount of fluid can be extracted from a relatively large fluid supply.

A fluid chamber can be a space or volume at a proximal end of a device, such as at a console housing, which can be used to contain pressurized or non-pressurized fluid (e.g., control fluid or injectate). Examples of specific types of fluid chambers include fluid reservoirs and pressure chambers. Optionally, a proximal end of a device may include one or multiple fluid reservoirs and pressure chambers, which can be provided for one or more different fluids including one or more injectates, one or more control fluids, or combinations of injectates and control fluids.

A fluid reservoir is generally a type of fluid chamber that can contain a fluid for a purpose of containing, transferring, holding, or storing a fluid, such as a fixed volume fluid chamber, and may be included as a permanent or removable (i.e., attachable and detachable) component of a console housing.

A pressure chamber or injection chamber can be a type of fluid chamber for containing one or more fluids (e.g., control fluid or injectate) for a purpose of placing the fluid under pressure to deliver the fluid through a lumen to a distal end of a shaft for ejection from an ejection orifice. Examples of pressure chambers include a syringe chamber and other variable volume spaces that can be used to contain and pressurize a fluid. Examples of variable volume pressure chambers include spaces that can exhibit a variable volume for increasing or decreasing the volume (and correspondingly decreasing or increasing pressure) within the variable volume chamber space. Such pressure chambers can include a plunger, piston, bellows, or other mechanisms. A pressure chamber can be pressurized by a pressure source attached to the plunger, bellows, or piston, etc., such that fluid contained in the pressure chamber is ejected under pressure. This pressurized fluid can be used for priming a device and/or for ejecting fluid from an ejection orifice for injection and/or to produce a control force, for example. A pressure source may be any source of energy (e.g., mechanical, electrical, hydraulically derived, pneumatically derived, or the like) such as a spring, solenoid, compressed air, manual syringe, electric power, hydraulic, pneumatic pressure sources, or the like. A pressure chamber may be a permanent or removable (i.e., attachable and detachable) component of a console housing.

Examples of consoles, console features and combinations of console features that can be useful according to the present description are identified in Applicants' copending U.S. Patent Application Publication No. 2006/0129125; U.S. Patent Publication No. 2009/0312696, filed Jun. 27, 2008 (Copa et al.); PCT patent application Serial No. U.S.09/06383, filed Dec. 4, 2009 (Rykhus et al.), titled "Method and Apparatus for Compensating for Injection Media Viscosity in a Pressurized Drug Injection System"; and PCT patent application Serial No. U.S.09/06381, filed Dec. 4, 2009 (Crank), titled, "Devices, Systems and Methods for Delivering Fluid to Tissue", the entire disclosures of which are incorporated herein by reference.

In communication with a proximal end of a device is an elongate shaft that extends from the proximal end (i.e., from a proximal shaft end), which is optionally removably connected to the console (or a component of the console such as a removable pressure chamber), to a distal end that can be placed in a patient during an injection procedure. A shaft can be of various designs, minimally including an injection lumen to carry injectate from a proximal end of the device to a distal end of the injection shaft. Shafts for needleless devices as described are also described in PCT patent application Serial No. U.S.09/06390, filed Dec. 4, 2009 (Crank et al.), titled "Devices, Systems, and Related Methods for Delivery of Fluid to Tissue"; and in PCT patent application Serial No. U.S.09/06384, filed Dec. 4, 2009 (Crank), titled "Needleless Injection Device Components, Systems, and Methods"; the entireties of which are both incorporated herein by reference.

Referring again to FIG. 1, a proximal or supply end 111 of the catheter tube or shaft 104 extends from a distal end of the injection chamber 108. The catheter tube 104 may be permanently attached or connected to the injection chamber 108 so that the tube 104 and chamber 108 are provided to the system either as a single component. Alternatively, catheter tube 104 may be attachable and detachable from injection chamber 108, such as with quick connection fittings, so that the injection chamber 108 and tube 104 are provided to the system as separate components. Catheter tube 104 further includes a delivery or distal end 112, which is generally opposite the proximal or supply end 111.

Catheter tube or shaft 104 is a generally continuous, elongated tube, which may include multiple lumens, attachments, or other components that may extend along all or part of the length of the tube 104. Catheter tube 104 may further comprise a number of different configurations, such as an endoscope or other catheter configuration, for example. Alternatively, catheter tube 104 can comprise a flexible, elongated tube 114 to allow for easy positioning of the delivery or distal end 112 within the patient. Supply or proximal end 111 of the tube 104 can be generally configured to attach to the injection chamber 108 and can include a quick-connect style connector. Alternatively, the proximal end 111 of the tube 104 can be permanently attached to the injection chamber 108.

Referring again to FIG. 1, delivery or distal end 112 of elongated tube 104 can comprise a number of different configurations, which can be selected to provide treatment to a certain location in the patient's body (e.g., a rectal treatment location, a gastrointestinal treatment location, a nasal treatment location, a bronchial treatment location, or an esophageal treatment location). The configuration of this distal end 112 is designed and/or selected to provide different types of treatment, such as can be provided by end-fire applicators or side-fire applicators.

An injection shaft minimally includes an injection lumen in communication with an injection orifice. The injection shaft can include structure such as sidewalls that define the injection lumen, the sidewalls being of sufficient strength to withstand operating pressures sufficient to deliver injectate from the injection orifice at an elevated pressure sufficient to cause the injectate to be ejected from the injection orifice to penetrate a tissue surface and become injected into and dispersed below the tissue surface. An injection shaft may be of a flexible material (e.g., a metal or polymeric tube) that can withstand such injection pressure, and may be prepared from exemplary materials capable of withstanding pressure of an injection, e.g., Nitinol, stainless steel, reinforced (e.g., braided) polymer, as also described elsewhere herein.

A basic version of a useful shaft of a device as described can be an "injection shaft" that includes a proximal end, a distal end, a sidewall that defines an internal lumen ("injection lumen"), and at least one injection orifice at the distal end in connection with the injection lumen.

An injection shaft can be any elongate structure capable of delivering fluid to a distal end of the injection shaft at a pressure suitable to inject tissue, as described. Exemplary injection shaft structures include relatively flexible hollow bodies having a distal end, a proximal end, sidewalls extending between the ends, and an internal lumen defined by interior surfaces of the sidewall. The injection lumen is in communication with one or more injection orifice at the distal end; the injection orifice may be as described herein, such as an aperture or bore in an injection shaft sidewall, an aperture or bore in a nozzle, end effector, injection head, or other structure in communication with the injection lumen.

An exemplary injection shaft can include a sidewall that defines an outer shaft surface and an inner injector lumen, these being of continuous and relatively uniform dimensions of inner diameter, outer diameter, and wall thickness, along an entire length of the injection shaft. Alternately, an injection shaft, injector lumen, or sidewall, may change dimensions (e.g., wall thickness) along the length of the injection shaft, with a larger wall thickness (e.g., greater outer diameter) at a proximal end and a thinner wall thickness (e.g., reduced outer diameter) at the distal end. A length of an injection shaft can be any length that functions to place a proximal end at a console and a distal end at a desired tissue location.

An injection shaft can be a component of a shaft of a needleless injection device or system. Other shaft components may include additional elongate shaft structures with desired functionality, a single example being a device referred to herein as "medical device shaft" or a "working shaft," which can be used to securely or moveably support or house an injection shaft. For instance, an injection shaft can be incorporated permanently or movably against or within a working shaft. In exemplary embodiments an injection shaft can be loosely contained in a working lumen of a working shaft to allow movement of the injection shaft length-wise and rotationally relative to the working shaft; an injection shaft may be capable of moving longitudinally within a working lumen to allow the injection lumen to be extended distally from an open end of a working lumen at a distal end of the working shaft.

An example of a "working shaft" or "medical device shaft" can be a shaft that is useful in conjunction with an injection shaft, to manipulate and place the injection orifice of an injection shaft at a desired location for treatment of tissue. A "working shaft" or "medical device shaft" can function to support the injection shaft and can optionally and preferably include any of a variety of optional functionalities such as steerability, an optical function, a tissue tensioner, or combinations of these, in addition to supporting the injection shaft.

An example of a particularly preferred working shaft can include features of a typical cystoscope, endoscope, ureteroscope, choledoscope, hysteroscope, catheter (e.g., urinary catheter), or the like, or other similar type of medical device shaft, including one or more feature of flexibility, an optical function, a steerable distal shaft end, and a working lumen.

A distal end of an injection shaft includes one or multiple injection orifices for ejecting fluid within a body of a patient. An injection orifice can be any form of opening, aperture, or orifice, such as an aperture or bore in an injection shaft sidewall, or an aperture or bore in a nozzle, end effector, injection head, or other structure in communication with an injection lumen. Injection orifices can be located at relative locations and orientations along a length or circumference of an injection shaft distal end to result in ejection and distribution of ejected fluid in different directions (e.g., circumferentially relative to the shaft), optionally or alternately at different distances along the length of the injection shaft. An injection orifice can be directed at any angle relative to a longitudinal axis of a shaft, such as perpendicular, angled toward a distal end, or angled toward a proximal end.

According to exemplary injection methods and devices, an injection orifice may be located on a proximal side of a distal end tip at a location that allows the injection orifice and adjacent injection shaft sidewall to contact a tissue surface as a longitudinal axis of a shaft that contains the injection orifice is positioned in an orientation that is parallel to the tissue surface. These device embodiments are sometimes referred to as "side-fire" devices, herein. As used herein, a "distal end tip" can be considered a location of a distal end of an injection shaft that is the farthest (most distal) feature of the injection shaft distal end. In certain embodiments of "side-fire" devices an injection orifice can be located a distance away from a distal end tip on a proximal side of the distal end tip so the injection orifice is located to contact tissue for injection by placing the shaft sidewall in contact with tissue.

According to certain exemplary devices, a distal end of a shaft (injection shaft, working shaft, or the like) can include a tissue tensioner, the tissue tensioner optionally being attached to the distal end of the shaft by a fastener that is attached to the tissue tensioner, such as part of a tissue tensioner assembly. A tissue tensioner can be located at a distal end of a shaft, somewhat near to an injection orifice, e.g., to be within a body lumen such as a urethra, e.g., a prostatic urethra, and near the injection orifice when the distal end of the shaft is installed in a patient for injection. For example a tissue tensioner can be located at a length-wise location along an injection shaft that is the same length-wise location as the length-wise location of an injection orifice.

A tissue tensioner can comprise an expandable surface, e.g., a continuous expandable surface such as an inflatable balloon, or a non-continuous expandable surface such as an expandable metal (or plastic) cage or the like. The expandable surface can exhibit an expanded state and a non-expanded state. According to exemplary methods, a tissue tensioner can be placed in a body lumen in a non-expanded state and expanded within the lumen to the expanded state. In the expanded state, the tissue tensioner contacts an internal surface of the lumen to hold the distal end of the shaft and an associated injection orifice in place relative to desired tissue for injection. The tissue tensioner can optionally produce tension or strain on the tissue in a manner that can affect the manner in which an injected fluid stream penetrates the tissue surface and becomes distributed in the tissue upon injection. A tissue tensioner can facilitate a good result upon injection of fluid through luminal tissue by ensuring that the luminal tissue is fixed and includes a desired amount of tension for receiving an injection.

Depending on the configuration of an injection orifice at a shaft of a device, or at an injector head, a tissue tensioner can be used to place a desired portion of tissue in (e.g., direct) contact with an injection orifice, i.e., a surface that contains an injection orifice. Alternately, a tissue tensioner can place a desired portion of tissue at a desired distance away from an injection orifice, e.g., in the instance of an injector head that includes two surfaces with a recessed surface including an injection orifice. The distance, if any, between an injection orifice and tissue, at injection, can be selected to affect properties of the injection, e.g., to affect the distance an injectate penetrates into tissue, the size of droplets formed beneath the tissue surface, and the pattern over which droplets of injectate are dispersed throughout tissue when injected. Other factors can also be adjusted to affect properties of the injection such as pressure and volume of injectate, size and shape of the injection orifice, etc.

Examples of tissue tensioners include inflatable balloons located at a shaft distal end near an injection orifice (e.g., at the same length-wise location as the injection orifice), and mechanically extendable structures such as paddles, protrusions, levers, metal or plastic cages, metal or plastic springs or spirals, and the like, any of which can include a surface that can be extended (e.g., mechanically) from a distal end of a working shaft or injection shaft to place pressure on internal tissue, e.g., on urethral tissue within the prostatic urethra or other luminal tissue. Tissue tensioners, device shafts, and related mechanisms and methods are described in Applicants' copending U.S. Patent Publication. No. 2006-0129125, and U.S. Patent Publication No. 2009-0312696, the entireties of which are both incorporated herein by reference.

A balloon or a mechanically extendable tissue tensioner can be inflated or extended at a location that is approximately at a length along a distal end of a shaft that is near an injection orifice, e.g., at a length-wise location that is the same as the length-wise location of the injection orifice. When used within a lumen such as a urethra, the tissue tensioner can push luminal tissue (e.g., urethral tissue) away from the distal end of the shaft in a manner that causes the luminal tissue and an injection orifice to contact each other. This can be done, for example, by a balloon expanding from an opposite side of a shaft relative to an injection orifice to place pressure on luminal tissue located opposite from an injection orifice and to cause the injection orifice to contact adjacent luminal tissue, optionally to produce pressure, strain, or tension on the luminal tissue opposite of the balloon. A mechanical tensioner may be extended from a distal end of a shaft by use of an actuating mechanism such as a mechanical connection between the tissue tensioner and the proximal end of a device, such as at a working shaft proximal end. An inflatable balloon may be extended from a distal end of a shaft by inflating the balloon with pressurized fluid such as liquid, air, other gaseous fluids, or the like.

Figure 2:
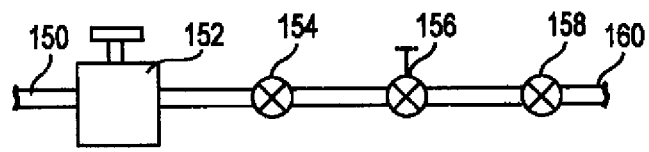
FIG. 2 is a schematic illustration of a control system that can be used to control inflation of a tissue tensioner or balloon of a fluid delivery system.

A number of different techniques and control systems can be used to inflate a balloon that is being used as a tensioner, as described herein. One exemplary system is illustrated in FIG. 2 and involves an automatic balloon inflation control system that provides for automated inflation based on volume control. In particular, this system includes an input tube or structure 150, a regulator 152, a first automatic valve or powered valve (e.g., a solenoid valve) 154, an adjustable valve 156, a second automatic valve (e.g., an automated pneumatic valve) or powered valve 158, and an output tube or structure 160. In operation, a material such as liquid, air, or gas is provided to the input structure 150, with the intention that this air or gas will be regulated by the control system to provide the desired inflation of the balloon or tensioner, which is operationally attached to the output structure 160. In one method, the steps include placing the first valve 154 in an open position and the second valve 158 in an open position to inflate the balloon. When the desired amount of air or gas has been transferred to the balloon, the first valve 154 will be closed. When it is desired to deflate the balloon, the second valve 158 will then vent to allow the balloon to deflate. These steps can be repeated to inflate and deflate the balloon, as desired.

The two-valve system of the type illustrated in FIG. 2 includes a first valve, which is either open or closed in both directions in its two positions. Another, second valve is either open or venting the downstream side to the atmosphere while the upstream side is closing. In this way, the first valve functions to allow flow in or to hold pressure back and the second valve functions to allow flow in or vent downstream (i.e., balloon) pressure while holding back upstream flow. This arrangement of valves is advantageous because it is capable of holding back upstream flow, allowing flow, holding downstream pressure, and venting the downstream pressure as desired for inflation and deflation of a balloon.

With this method, the total volume of gas or air that flows to the balloon is controllable by controlling the flow rate with the regulator 152 and/or the adjustable valve 156 and the corresponding time that the gas or air is allowed to flow to the balloon. This is performed during the duration of the step that involves having the first and second valves 154, 158 in their open positions.

Although the system described relative to FIG. 2 includes a regulator, two valves or automatic valves, and an adjustable valve, it is understood that the system can instead include only two of these components, depending on certain system parameters. Depending on the consistency of the supply pressure, exemplary combinations of the components include the following: (1) a regulator, an adjustable valve, and two 2-position valves; (2) a regulator, an adjustable valve, and one 3-position valve; (3) a regulator and a 3-position valve; (4) a regulator and two 2-position valves; (5) an adjustable valve and a 3-position valve (for a constant supply pressure); (6) an adjustable valve and two 2-position valves (for a constant supply pressure); (7) one 3-position valve (for a constant supply pressure); and (8) two 2-position valves (for a constant supply pressure). The adjustable parameter in these configurations is the time that the fluid path is open.

Figure 3:
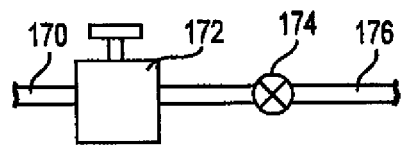
FIG. 3 is a schematic illustration of another control system that can be used to control inflation of a tissue tensioner or balloon of a fluid delivery system.

Another exemplary system that can be used to inflate a balloon that is being used as a tensioner is illustrated in FIG. 3 and involves an automatic balloon inflation control system that provides for automated inflation based on pressure control. In particular, this system includes an input tube or structure 170, a regulator 172, an automatic valve (e.g., an automated pneumatic valve) or solenoid 174, and an output tube or structure 176. In operation, a material such as fluid, air, or gas is provided to the input structure 170, with the intention that this air or gas will be regulated by the control system to provide the desired inflation of the balloon or tensioner, which is operationally attached to the output structure 176. In one method, the steps include moving the valve 174 from its closed position to its open position, allowing the balloon to be pressurized by the fluid to a pressure controlled by the regulator 172. When it is desired to deflate the balloon, the valve 174 will then vent, which can be accomplished, for example, with a 2-position valve that blocks the upstream flow and vents the downstream pressure in one position, and that allows flow from upstream to downstream in another position. These steps can be repeated to inflate and deflate the balloon, as desired. Thus, this system uses the regulator 172 to control the pressure transmitted to the balloon.

Figure 4:
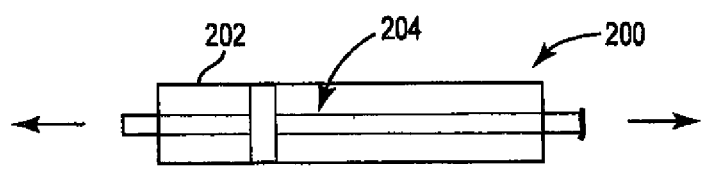
FIGS. 4 and 5 are front, partial schematic views of a system for achieving relatively high jet stagnation pressure in a short time for a fluid delivery system of the invention.
Figure 5:
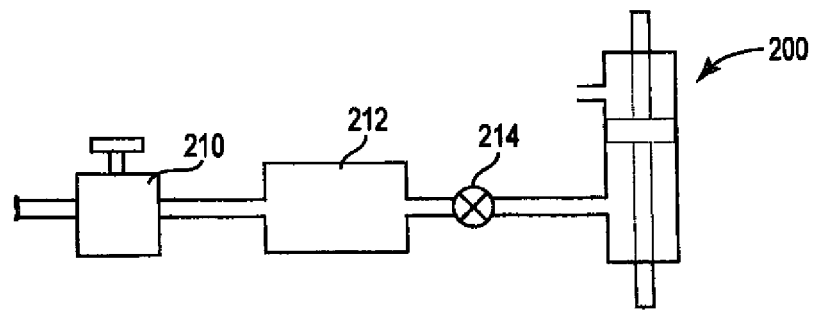

When using the various devices of the system to inject pressurized fluid into tissue, it can be advantageous to get the fluid or "jet" up to a desired operational speed quickly. In this way, a larger amount of the fluid dose can be ejected at a speed that is sufficient to penetrate the target tissue. This can be particularly beneficial when administering relatively small doses of the fluid. To that end, FIGS. 4 and 5 illustrate a device and method for achieving a higher jet stagnation pressure in less time in order to have better fluid penetration in the target tissue. In particular, FIG. 4 illustrates an air or gas cylinder 200 that drives the fluid injection. Cylinder 200 includes an outer cylindrical wall 202 and a plunger 204. FIG. 5 illustrates this cylinder 200 in combination with a regulator 210, a reservoir 212, which may contain a volume of compressed air or gas, and a valve 214. The valve 214 controls the flow of fluid to the firing/injection side of the cylinder 200. In order to achieve a faster response time for the jet, the side of the cylinder 200 that does not drive the injection is pressurized, to return the cylinder 200 to its starting position, at which point it can be vented. The reservoir 212 of compressed air or gas, which is positioned just upstream of the valve 214, provides an impulsive force for quick acceleration upon opening of the upstream valve 214. In general, increasing the product of pressure and volume upstream from the regulator 210 will also reduce jet response time to give faster flow acceleration.

An alternate way of accomplishing the quick acceleration of a fluid jet is to use gas power and have a regulator that could modulate the acceleration of the air cylinder. However, this system would require very fast response times in the control of the regulator.

Figure 10:
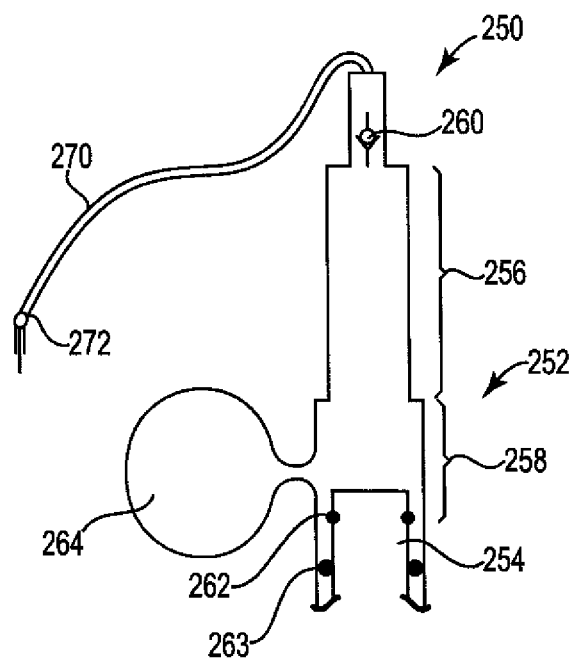
FIG. 10 is a front view of a high-pressure fluid injection system including a rechargeable injection chamber including a check valve.

An exemplary embodiment of a high-pressure fluid injection system 250 including a rechargeable injection chamber 252 with a check valve 260 is illustrated in FIG. 10. The injection chamber 252 includes a plunger 254, a high-pressure zone 256, a low-pressure zone 258, the check valve 260, and one or more seals 262, 263 in operative engagement with the plunger 254. In particular, seal 262 can be considered to be a high-pressure seal, while seal 263 can be considered to be a relatively low-pressure seal. When the system 250 includes a check valve 260, as shown, the plunger 254 can advance so that the high-pressure seal 262 engages with the high-pressure zone 256. This causes the check valve 260 to open. When the plunger 254 stops its forward movement, the check valve 260 closes. When the plunger 254 is retracted, a vacuum is then pulled in the high-pressure zone 256, which causes the high-pressure seal 262 to disengage from the high-pressure zone 256 and injectate then traverses from a reservoir 264.

In the above-described embodiment, a check valve 260 is used; however, check valves can be expensive and can increase manufacturing time and costs. Thus, certain embodiments of system 250 do not require a check valve. In one embodiment, the injection chamber can be equipped with a plunger configured to retract relatively quickly in order to reduce the time allowed for external fluid within the system to be pulled into the injection chamber. In addition, the size (e.g., small) or shape of the catheter lumen or tubing and corresponding tip orifices can assist in controlling fluid flow by providing a level of flow resistance. These beneficial design features of the chamber and lumen configurations can permit control of the fluid flow without the use of a check valve. As such, the steps discussed above that require the opening and closing of the check valve 260 are not necessary. In addition, various configurations of an injection tube 270 (which includes a central lumen), plunger 254, injectate orifices 272, and injection chamber 252 can be included to control the fluid flow without the use of the check valve 260.

Figure 6:
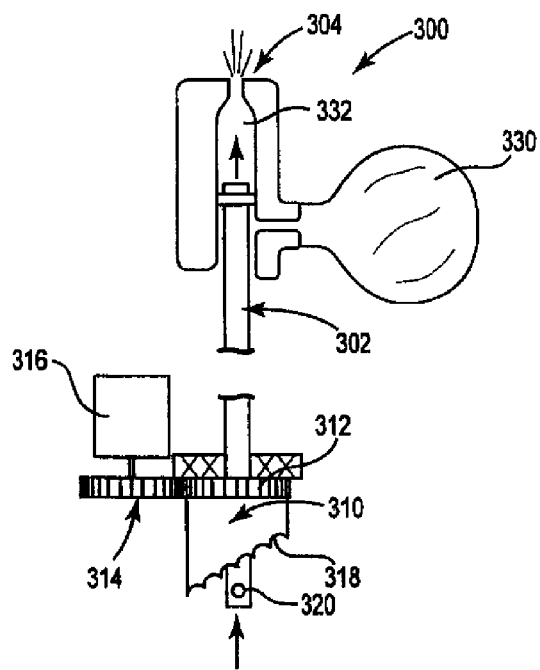
FIGS. 6-9 are front views of portions of fluid delivery systems of the invention, which include devices for controlling the volume of fluid that is ejected from the delivery systems.
Figure 8:
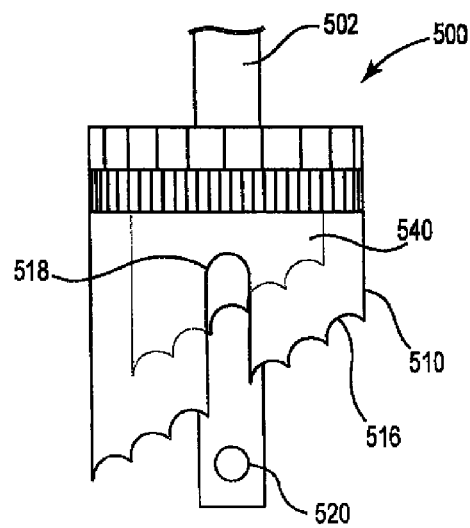

FIGS. 6-9 illustrate systems and devices for controlling the volume of fluid that is ejected from an injection system, in accordance with the invention. FIG. 6 illustrates a portion of an injection system 300, which generally includes a shaft 302, the movement of which determines the volume of fluid that is displaced or ejected from an end 304 of the system. This fluid can be provided by a reservoir 330, for example, which can include a syringe or other fluid container. In particular, the distance that the shaft 302 travels in a linear direction will determine the volume of fluid that will be ejected from the system. The system 300 further includes a rotating, stepped stop member 310 that is positioned generally concentrically about the shaft 302. The member 310 is further attached at one end to a first gear 312, which in turn is engaged with a second gear 314. The second gear 314 is operationally attached to a motor 316, which thereby drives the rotational movement of the member 310 via its attached gear 312. Alternatively, many different types of gears could be used in place of those illustrated, along with various types of belts, chains, etc., and combinations thereof, in an automated system. In addition, the rotating stepped stops can be positioned manually or in an automated manner, as desired.

The member 310 further includes a series of grooves or stops 318 spaced around its circumference, where each of the grooves or stops 318 is arranged in a step-like or angular configuration, as shown. Further, the end of the shaft 302 that is extendible beyond the member 310 includes a shaft protrusion 320 that is at least long enough to be able to engage with the grooves or stops 318 when the shaft 302 moves linearly upward (relative to this figure). The protrusion 320 may extend from one or both sides of the shaft 302, although its engagement with the member 310 may be more secure when it protrudes from both sides of the shaft 302 than when it protrudes from one side of the shaft. The protrusions 320 may be formed by pressing dowel pins or other similar devices through a hole that extends at least partially through the shaft 302.

In operation, fluid is provided to a channel 332 adjacent the end 304 of the system from which the fluid will be ejected. The member 310 is rotated either by an automatic system or by manual adjustment to place it in a desired location that is associated with a certain volume of fluid that is intended to be ejected from the end 304. That is, the system is configured such that particular positions of the member 310 are associated with a particular fluid administration. A force is then placed on the shaft 302 at the end closest to the protrusion or protrusions 320 to move the shaft 302 in a linear direction toward the end 304. Springs, pneumatic cylinders, magnetic forces, and other motive forces may generate this force. This movement of the shaft 302 will continue until one or more protrusions 320 engage with one or more corresponding grooves or stops 316, thereby preventing any further linear movement of the shaft. In this way, the travel of the shaft is controlled, thereby controlling the volume of fluid that is displaced from the system.

Figure 7:
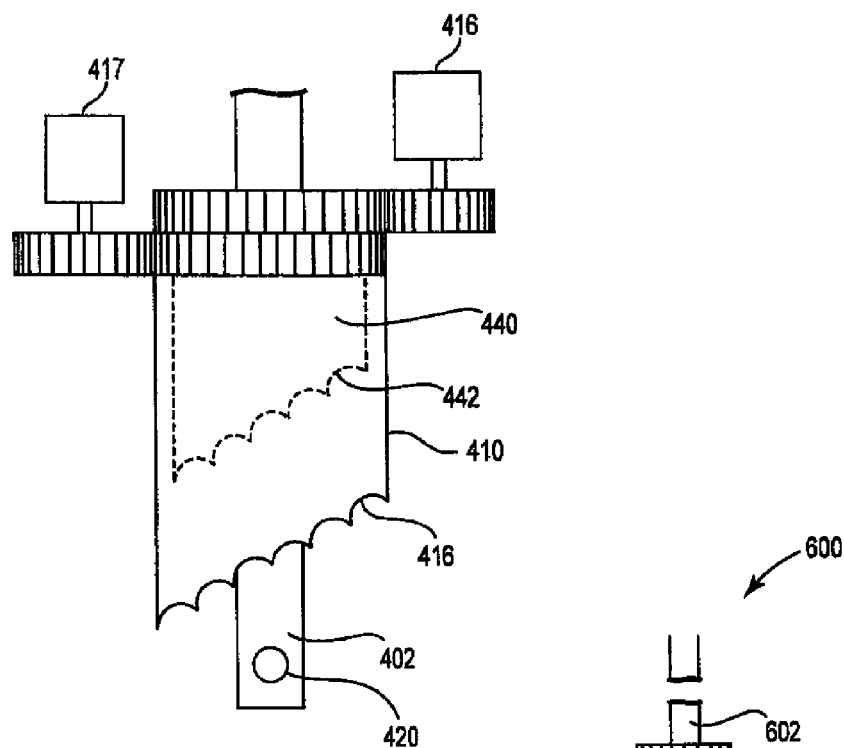

FIG. 7 illustrates another exemplary embodiment of a system of the type illustrated in FIG. 6, which includes two rotating, stepped stop members 410, 440 which are generally concentrically positioned relative to each other. The system further includes a shaft 402 with one or more protrusions 420 that will be adjacent the members 410, 440. This system further includes two motors 416, 417, wherein the motor 417 rotates the member 410 and the motor 418 rotates the member 440. As with the embodiment of FIG. 6, the shaft protrusion(s) 420 of this embodiment also are engageable with grooves 416, 422 to control the movement of the shaft 402 in a linear direction, thereby controlling the volume of fluid that is ejected from the system.

Another exemplary embodiment of a system similar to those discussed above is a system 500 illustrated in FIG. 8, which includes a shaft 502 having a shaft protrusion 520 at one end, and two stepped stop members 510, 540 that are positioned generally concentrically relative to each other and the shaft 502. As shown, the internal member 540 includes a series of grooves as are generally described above; however, the outer member 510 includes both small grooves 516 and at least one relatively long or tall groove 518. In this way, the protrusion 520 can engage with the small grooves 516, when desired, but when it is desired to allow further movement of the shaft, the member 540 can be rotated so that the protrusion 520 can slide into the groove 518 to be able to engage with the grooves of the internal member 540.

Figure 9:
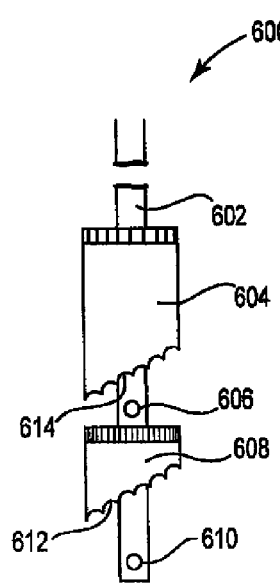

Another exemplary embodiment of a stepped stop arrangement is illustrated in FIG. 9, in which a system 600 includes two stepped stop members 604, 608 that are arranged in a series configuration along a shaft 602. The shaft 602 includes two protrusions 606, 610, which are positioned to engage with grooves 614, 612 of the members 604, 608, respectively.

In general, multiple rotating stepped stops of the types described above may be used when positioned concentrically or serially with respect to each other. The stops may be rotated by a single driving means, where some type of engagement selection would be provided (e.g., a two-way ratchet for directional engagement selection), or by separate means. To prevent both stops from simultaneously acting on the shaft and conflicting with each other when rotating, stepped stop is needed, the other can be rotated to a position such that its corresponding shaft protrusions will not engage it. Thus, the long slot or groove described above relative to FIG. 8 can provide the "step" for which the travel of the shaft protrusion is insufficient to reach. The rotating stepped stops can be rotated with electrical motors, pneumatic motors, or by hand, and each modality can use belts and pulleys, chains and sprockets, or gear sets.

Figure 11:
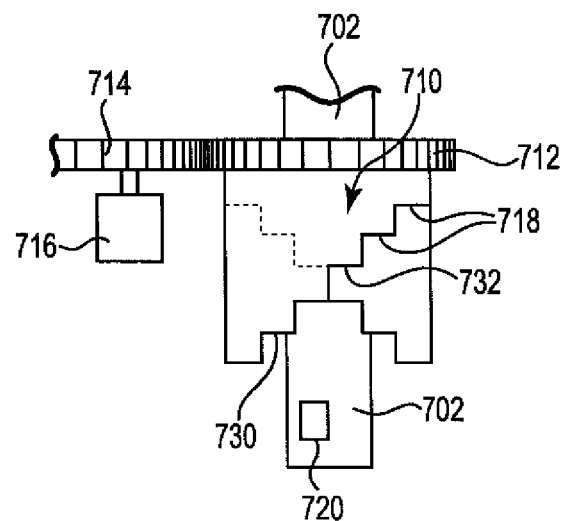
FIG. 11 is a front view of a portion of a high-pressure fluid delivery system having stepped dosage control.

Another exemplary embodiment of a stepped stop arrangement is illustrated in FIG. 11. In this embodiment, a system 700 can optimize the use of the injectate fluid, thereby reducing the amount of injectate fluid that is wasted in an injection lumen and/or other components of the system 700. In particular, system 700 includes a shaft 702, the movement of which determines the volume of fluid that is displaced from an end of the system. This fluid can be provided by a reservoir, which can include a syringe or other fluid container. The distance that the shaft 702 travels determines the volume of fluid that will be ejected from the system 700. The system 700 further includes a rotating, stepped stop member 710 that is positioned generally concentrically about the shaft 702. The member 710 is further attached at one end to a first gear 712, which in turn is engaged with a second gear 714. The second gear is operationally attached to a motor 716, which thereby drives the rotational movement of the stepped member 710 via its attached gear 712. Alternatively, many different types of gears could be used in place of those illustrated, along with various types of belts, chains, etc., and combinations thereof, in an automated system. In addition, the rotating stepped stops can be positioned manually or in an automated manner, as desired.

The member 710 includes a series of steps 718 arranged in a step-like configuration and spaced around at least a portion of its circumference. As a part of the system 700, the end of the shaft 702 that extends beyond the stepped member 710 includes a shaft protrusion 720 that extends at least far enough from the outer surface of the shaft 702 that it can engage with the steps 718 when the shaft 702 moves linearly upward (with respect to this figure). Although one protrusion is shown, a system 700 may include multiple protrusions 720 extending from one or more areas around the shaft 702. The protrusions 720 may be formed by pressing dowel pins or other similar devices through a hole that extends at least partially through the shaft 702.

In operation, fluid is provided to a channel of the system 700 at and end of the shaft 702 that is opposite that end having the protrusions 720. The member 710 is rotated either by an automatic system or by manual adjustment to place it in a desired location that is associated with a desired amount of fluid that is to be ejected from the system 700. In particular, the system is configured such that the protrusion 720 travels forward until it stops against one of the steps 718, then the load is removed, allowing the member 710 to rotate to a new position. Movement to this new or next sequential position (e.g., higher, in this figure) allows the protrusion 720 to continue traveling upward, which allows more injectate to be ejected without having to retract a distal end of the device (e.g., an injectate shaft, lumen tip, and the like). For one example, the protrusion 720 can be advanced so that it stops against a step designated by reference number 730 to eject a certain dosage of fluid. The member 710 can then rotate (with no load from the protrusion) so that the protrusion 720 aligns with a step designated by reference number 732, thereby providing an additional dosage of injectate. The protrusion 720 can advance even further relative to the steps 718, if desired, in order to eject yet another dosage of injectate. In this way, a controlled or predefined application and use of fluid dosage is provided.

In embodiments of the member 710, the number, depth, length, etc. of the steps 718 can be designed and provided to control the amount of fluid released per dosage, and can vary widely depending on the particular treatment and dosage requirements. Further, the number of steps 718 and corresponding defined dosages can vary in accordance with the particular desired performance of the system. In addition, it is contemplated that various motors, plungers, and like devices and techniques can be used to facilitate the rotation and controlled fluid dosage of the system 700. Further, the components of the stepped rotating stop 710 can be in operative or fluid communication with other components of the system 700, including a fluid reservoir or source, plunger, and the like. In addition, the injection chamber or reservoir can be charged with the total amount of injectate that is to be injected, or it can instead be charged with a limited amount of injectate so that when a predefined injectate dose has been ejected, the plunger or source can be retracted and recharged.

Other stepped or controlled dosage devices, structures, and techniques can be employed with the systems of the invention to achieve the objective of controlling fluid dosage and minimizing waste of injectate fluid within the system. For example, non-rotating, pre-defined stepping devices, pre-defined actuators, and the like, can be used with the devices and systems of the invention.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A fluid injection system comprising:
a channel at a distal end of the system, the channel comprising an input end and an outlet end;
a shaft positioned at least partially within the channel and comprising a proximal shaft end, a closed distal shaft end, and at least one protrusion extending from an outer surface of the shaft adjacent the proximal shaft end;
a rotatable, stepped stop member comprising multiple step portions along a proximal edge of the member, wherein the stop member is positioned concentrically around the shaft, and wherein the shaft is linearly translatable within the channel in a distal direction for engagement of the at least one protrusion with at least one of the step portions and for pushing fluid from the outlet end of the channel; and
a reservoir in fluid communication with the channel between the closed distal shaft end and the outlet end of the channel.

2. The fluid injection system of claim 1, wherein the stepped stop member is manually rotatable.

3. The fluid injection system of claim 1, wherein the distal shaft end comprises a first position in which a volume of fluid is injectable into the channel and a second position in which the at least one protrusion is engaged with at least one of the step portions, wherein the distal shaft end is linearly moveable from the first position to the second position for ejecting at least a portion of the volume of fluid from the outlet end of the channel.

4. The fluid injection system of claim 1, wherein each of the multiple step portions comprises a flat step portion.

5. The fluid injection system of claim 1, wherein the stepped stop member is automatically rotatable.

6. The fluid injection system of claim 5, further comprising a motor operatively engaged with the stepped stop member to provide its automatic rotation.

7. The fluid injection system of claim 1, wherein the distal shaft end is in fluid communication with the channel.

8. The fluid injection system of claim 7, wherein the distal shaft end is linearly moveable relative to a length of the channel.

* * * * *